(12) United States Patent
Mentrup et al.

(10) Patent No.: US 9,615,808 B2
(45) Date of Patent: Apr. 11, 2017

(54) METHOD AND RADIOGRAPHY SYSTEM FOR GRID-LIKE CONTRAST ENHANCEMENT

(71) Applicant: KONINKLIJKE PHILIPS N.V., Eindhoven (NL)

(72) Inventors: Detlef Mentrup, Hamburg (DE); Sascha Andreas Jockel, Hamburg (DE); Hanns-Ingo Maack, Norderstedt (DE); Bernd Menser, Hauset (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/554,173

(22) Filed: Nov. 26, 2014

(65) Prior Publication Data

US 2015/0342554 A1    Dec. 3, 2015

Related U.S. Application Data

(60) Provisional application No. 62/003,163, filed on May 27, 2014.

(51) Int. Cl.
  *G06K 9/00* (2006.01)
  *A61B 6/00* (2006.01)
(52) U.S. Cl.
  CPC .......... *A61B 6/5282* (2013.01); *A61B 6/4291* (2013.01); *A61B 6/582* (2013.01)

(58) Field of Classification Search
  USPC .................................................. 382/128–134
  See application file for complete search history.

(56) References Cited

U.S. PATENT DOCUMENTS

| | | | |
|---|---|---|---|
| 5,666,391 A | 9/1997 | Ohnesorge et al. | |
| 2003/0103666 A1* | 6/2003 | Edic | G06T 5/003 |
| | | | 382/132 |
| 2005/0031182 A1* | 2/2005 | Inoue | G06T 5/002 |
| | | | 382/132 |
| 2010/0020933 A1* | 1/2010 | Topfer | G06T 5/50 |
| | | | 378/98.11 |
| 2010/0027867 A1* | 2/2010 | Bernhardt | A61B 6/00 |
| | | | 382/132 |

FOREIGN PATENT DOCUMENTS

| | | |
|---|---|---|
| DE | 102012200150 A1 | 7/2013 |
| EP | 2120040 A1 | 11/2009 |
| WO | 2007148263 A1 | 12/2007 |
| WO | 2013192600 A1 | 12/2013 |

\* cited by examiner

*Primary Examiner* — Alex Liew (57) ABSTRACT

A method and system for processing a radiography image derived from an X-ray radiation passing through an object. The method includes acts of estimating, based on the radiography image, a scatter signal present in said radiography image; calculating, based on the estimated scatter signal, a scatter removal signal indicative of a scattered radiation removable from the X-ray radiation passing through the object by a reference anti-scatter device; and correcting the radiography image based on the scatter removal signal.

20 Claims, 6 Drawing Sheets

METHOD AND RADIOGRAPHY SYSTEM FOR GRID-LIKE CONTRAST ENHANCEMENT

CROSS-REFERENCE TO PRIOR APPLICATIONS

This application claims the benefit of U.S. application Ser. No. 62/003,163, filed on May 27, 2014. These applications are hereby incorporated by reference herein.

FIELD OF THE INVENTION

The invention relates to a method for processing a radiography image derived from an X-ray radiation passing through an object, a radiography system for performing such method and a computer program, stored on a computer readable medium, arranged for performing the method when run on a computer.

BACKGROUND OF THE INVENTION

When X-ray radiation penetrates an object such as a patient to be imaged, scattered radiation is generated. Scattered radiation causes a reduction of contrast in X-ray images. Anti-scatter devices, for example anti-scatter grids, have the quality of attenuating scattered radiation while allowing non-scattered radiation to pass. Therefore anti-scatter devices are typically employed to counteract the contrast reduction caused by scattered radiation. However, the use of anti-scatter devices, and notably the use of anti-scatter grids, imposes several requirements and hence restrictions on clinical workflow.

SUMMARY OF THE INVENTION

Thus, there is need for a method for radiography image processing providing contrast enhancement while circumventing clinical workflow restrictions.

The object of the present invention is solved by the subject-matter of the independent claims, wherein further embodiments are incorporated in the dependent claims.

It should be noted that the following described aspects of the invention apply also for the radiography system and the computer program according to the invention.

According to a first aspect of the present invention, a method for processing a radiography image derived from an X-ray radiation passing through an object is provided. Such method comprises a step for estimating, based on the radiography image, a scatter signal present in said radiography image; a step for calculating, based on the estimated scatter signal, a scatter removal signal indicative of a scattered radiation removable from the X-ray radiation passing through the object by a reference anti-scatter device; and a step for correcting the radiography image based on the scatter removal signal.

The method according to the invention comprises calculating, based on an estimated scatter signal, a scatter removal signal. This scatter removal signal is indicative of a scattered radiation removable from the X-ray radiation passing through the object by a reference anti-scatter device, i.e. indicative of the scattered radiation that would be removed from such X-ray radiation in case the reference anti-scatter device would be physically employed. Hence the method according to the present invention is capable of realizing the contrast enhancing effect of said reference anti-scatter device without physically employing it. Consequently the method according to the present invention advantageously and effectively circumvents workflow restrictions that go along with employing an anti-scatter device and more notably an anti-scatter grid. Such workflow restriction for example relate to proper position and alignment of the anti-scatter device with respect to an X-ray beam. As a consequence the present invention particularly allows for useful application in free X-ray exposures such as bedside chest radiography in which a fixed geometry is absent. Likewise the present invention improves workflow in intensive care units in which the weight and bulk of the anti-scatter device is an obstacle.

In this text an anti-scatter device encompasses an anti-scatter grid, air gap technology and/or a slotscan system.

Furthermore, the method according to the present invention advantageously prevents artifacts that would be obtained when increasing image contrast via processing the radiography image with a high-pass frequency filter. For example, degradation of signal-to-noise-ratio in low-dose areas, which artifact, is effectively circumvented by the present invention.

According to a second aspect of the present invention, a radiography system is provided for performing the method according to the present invention.

In a preferred embodiment of the radiography system according to the present invention, the radiography system is arranged for using a reference anti-scatter grid when performing the step of calculating the scatter removal.

In another preferred embodiment of the radiography system according to the present invention, the radiography system is arranged for using calibration data acquired upfront with the reference anti-scatter device when performing the step of calculating the scatter removal signal. This embodiment advantageously increases the accuracy of calculating the scatter removal signal.

In another preferred embodiment of the radiography system according to the present invention, the radiography system is arranged for performing a step for specifying a quality of the reference anti-scatter device by user manual interaction, as part of the step for calculating the scatter removal signal. For example, the radiography system may offer the user to select, via a user interface, from a plurality of reference anti-scatter devices a particular reference anti-scatter device, such as a reference anti-scatter grid, having a quality matching the clinical application at hand. Moreover, the radiography system may offer the user to subsequently specify a selectivity and/or a contrast improvement ratio for such reference anti-scatter grid. This embodiment has the advantage of increasing clinical flexibility. Alternatively, the radiography system may automatically select the type of reference anti-scatter device and its qualities in dependence of the clinical application at hand.

In another preferred embodiment of the radiography system according to the present invention, the radiography system is arranged for performing a step for retrieving from a database representative scatter kernels in relation to respective local properties of the radiography image and subsequently superpositioning said scatter kernels for estimating the scatter signal, as part of the step for estimating the scatter signal based on the radiography image.

In another preferred embodiment of the radiography system according to the present invention, the radiography system is arranged for using a respective local signal of the radiography image and a respective local spatial gradient of said respective local signal when performing the step of retrieving from a database representative scatter kernels. For example, such local signal may be determined on a per pixel basis. The respective local signal of the radiography image and its local spatial gradient are particularly suitable for use with sphere based scatter modelling. The respective local signal of the radiography image and the local spatial gradient thereof are unique, and will vary from one body part to another, from one image to the other, from one patient to another and more generally from one pixel to another. Therefore this embodiment advantageously enables patient and region specific scatter correction. For example, contrast enhancement will be stronger for obese patients than for slim patients. Likewise, for some radiography image of a patient's chest, contrast enhancement will be stronger for areas with high scatter fraction, such as the mediastinum and abdomen, and will be less strong for areas with less high scatter fraction, such as the lung.

In another preferred embodiment of the radiography system according to the present invention, the radiography system is arranged for using scatter kernels that are generated upfront by Monte Carlo simulation, when performing the step of retrieving from a database representative scatter kernels. Monte Carlo simulation has proven as an accurate method for precise numerical approximation. For the purpose of scatter estimation, Monte Carlo simulation of the passage of X-rays through a range of material levels in dependence of a range of tube voltages may be employed. A particularly suitable material for that purpose is water. However, Monte Carlo simulation does involve a significant computational effort. This embodiment is advantageous in that clinical workflow is not hampered by such computational expense. Namely, this embodiment effectively suggests making such computation effort in advance, to store the results in aforementioned database, and to subsequently re-use those result via accessing the database.

In another preferred embodiment of the radiography system according to the present invention, the radiography system is arranged for performing the step of estimating the scatter using a resolution lower than a resolution of the radiography image. This embodiment has the advantage of reducing computation time without compromising accuracy. Namely, the estimated scatter signal is smoothly varying and dominated by low frequency components. Therefore, estimation is well feasible at a resolution that is low relative to the resolution of the image.

U.S. Pat. No. 8,000,435 B2 discloses the generation of scatter kernels and is incorporated herein by reference.

In another preferred embodiment of the radiography system according to the present invention, the radiography system is arranged for performing a step of increasing the resolution of the estimated scatter signal to a level equal to the resolution of the radiography image. This embodiment advantageously improves correcting the radiography image for scatter based on the calibrated estimated scatter signal.

In another preferred embodiment of the radiography system according to the present invention, the radiography system is arranged for performing a step of specifying via segmentation an anatomical area for which contrast enhancement is particularly. Such segmentation may be initiated by user manual interaction via a user interface. Alternatively it may be performed automatically. The effect of such segmentation, either manually or automatically, is in locally adapting a quality of the reference anti-scatter device towards locally higher contrast enhancement. For example, in terms of a reference anti-scatter grid, such segmentation locally increases selectivity and/or contrast improvement ratio. This embodiment has the advantage of obtaining optimum contrast enhancement for the anatomical area that is clinically of most interest without affecting other anatomical areas negatively in terms of noise.

In another preferred embodiment of the radiography system according to the present invention, the radiography system is arranged for performing a step of subtracting the estimated scatter signal from the radiography image, when performing the step of correcting the radiography image based on the scatter removal signal. This embodiment is advantageous in that it minimizes edge artifacts.

In another preferred embodiment of the radiography system according to the present invention, the radiography system is arranged for performing a step of multiplying the radiography image with a scatter signal fraction incorporating the estimated scatter signal, when performing the step of correcting the radiography image based on the scatter removal signal.

According to a third aspect of the present invention, a computer program is provided, which computer program is stored on a computer readable medium and arranged for performing when run on a computer.

DETAILED DESCRIPTION OF THE EMBODIMENTS

Hereinafter, equal reference numbers as used throughout the various drawings denote identical features.

Figure 1:
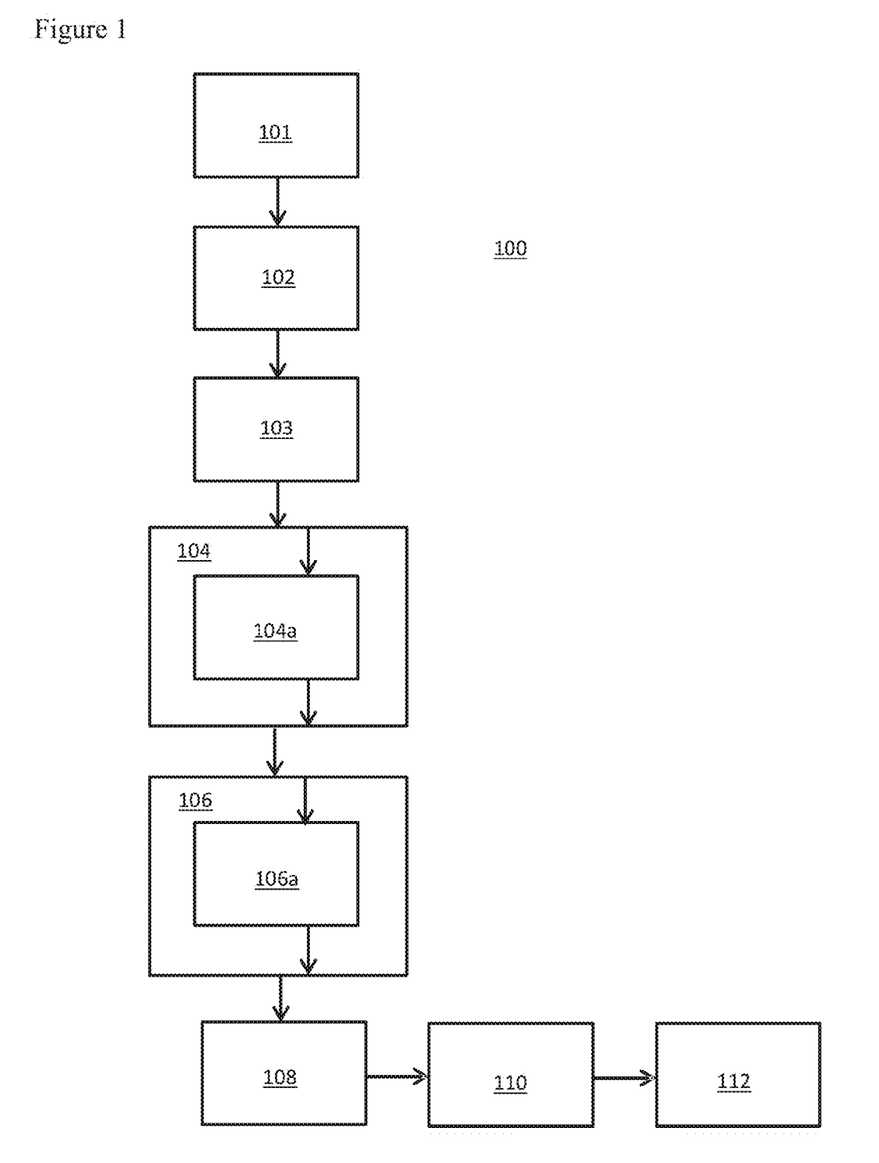
FIG. 1 schematically depicts the method according to the present invention.

Referring to FIG. 1, the method 100 according to the present invention is schematically displayed. Such method 100 processing a radiography image derived from an X-ray radiation passing through an object comprises a step 104 for estimating, based on the radiography image, a scatter signal present in said radiography image; a step 106 for calculating, based on the estimated scatter signal, a scatter removal signal indicative of a scattered radiation removable from the X-ray radiation passing through the object by a reference anti-scatter device; and a step 110 for correcting the radiography image based on the scatter removal signal.

Figure 2:
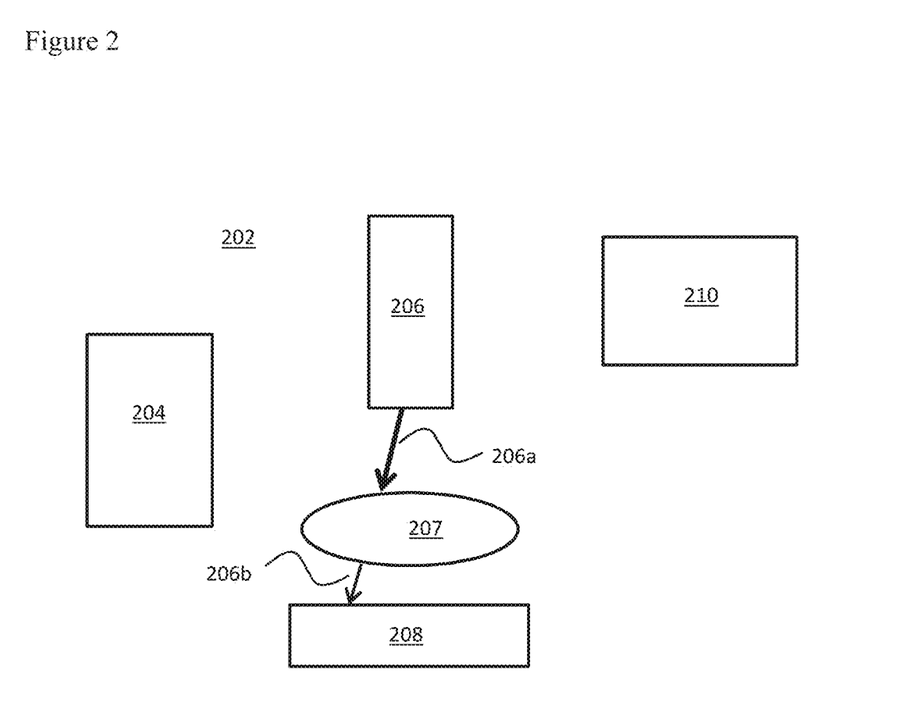
FIG. 2 schematically displays the system according to the invention.

Referring to FIG. 2, the radiography system 202 according to the invention for performing method 100 is schematically displayed. An example radiography system 202 comprises a controller 204 for performing the method 100. Alternatively a processor (not shown) may be used for that purpose. Radiography system 202 may comprise an X-ray tube 206, known per se to the person skilled in the art, for submitting an X-ray radiation 206a towards an object 207 to be imaged. Radiography system 202 may furthermore comprise an X-ray detector 208, known per se to the person skilled in the art, for detecting an X-ray radiation 206b having passed the object 207. The controller 204 may be remotely arranged from both X-ray tube 206 and X-ray detector 208. In another example, radiography system 202 comprises a user interface 210 for user manual interaction.

Referring to FIG. 1, the radiography image as processed by the method 100 comprises clean raw image data. In a specific example, radiography system 202 is arranged for performing a step 101 for generating raw image data and a step 102 for subsequently pre-processing such raw image data, i.e. for correcting detector related artifacts, in order to generate clean raw image data constituting the radiography image. Radiography system 200 may be arranged to perform steps 101 and 102 in either linear or logarithmic data space.

In an example, radiography system 202 is arranged for using a reference anti-scatter grid when performing step 106. Herein, radiography system may employ any type of reference anti-scatter grid. More specifically, such reference anti-scatter grid may have a selectivity in the range of 2 to 12 and/or a contrast improvement ratio in the range of 1.1 to 4.4. These quantities are usually denoted by $\Sigma$ and K, respectively, and are for example defined in IEC standard 60627.

Figure 4:
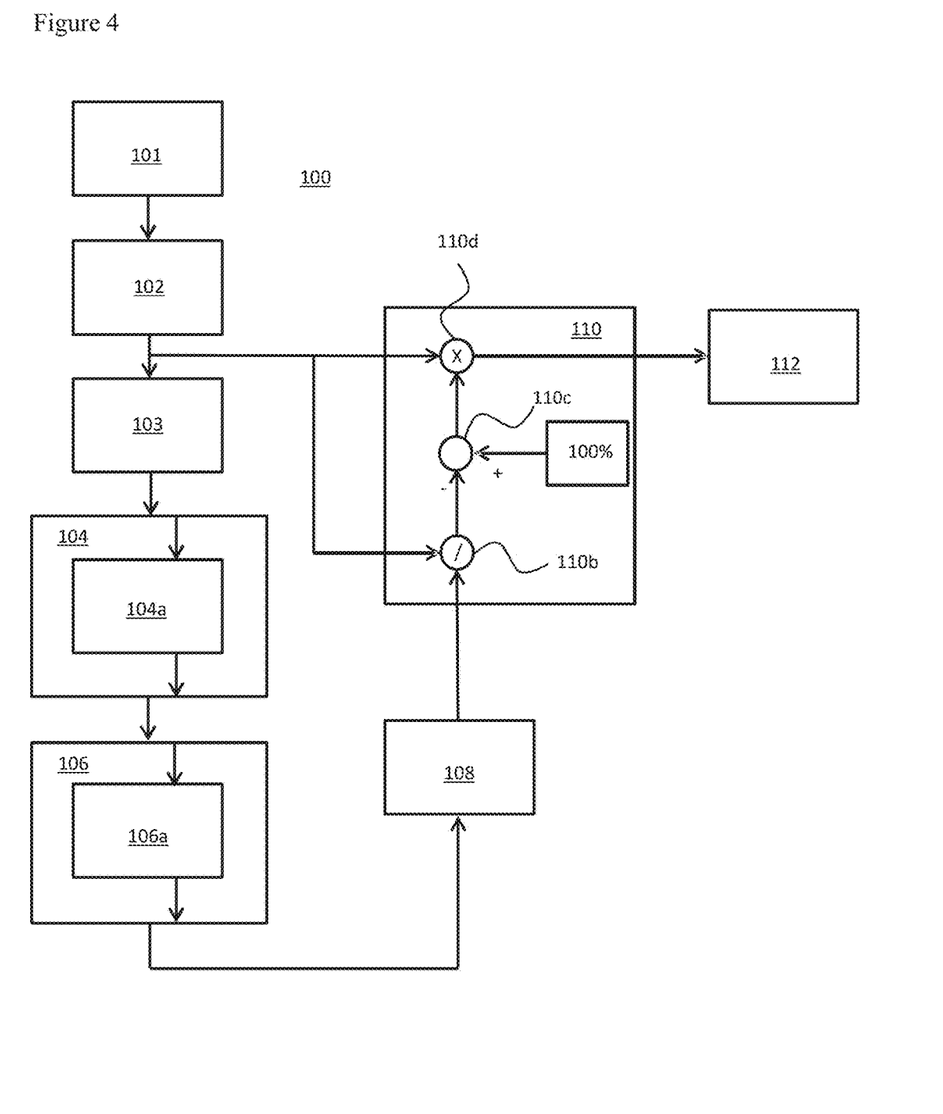
FIG. 4 schematically depicts another method performable by an embodiment of the radiography system according to the present invention.

In another example, radiography system 202 is arranged for performing step 106 using calibration data acquired upfront with the reference anti-scatter device. Referring to FIG. 4, results of an experimental verification of such calibration data are displayed for an example in which the reference anti-scatter device is a reference anti-scatter grid having selectivity 5.6 and contrast improvement ratio 3.4.

In a specific example, radiography system 202 is arranged for performing a step 106a for specifying a quality of the reference anti-scatter device by user manual interaction. For example, the radiography system 202 may enable the user, via user the interface 210, to select as reference anti-scatter device for example a reference anti-scatter grid, and to subsequently select a value for the selectivity and/or the contrast improvement ratio associated with such reference anti-scatter grid.

In another specific example step, radiography system 202 is arranged for performing, as part of step 104, a step 104a for retrieving from a database representative scatter kernels in relation to respective local properties of the radiography image and for subsequently superpositioning said scatter kernels for estimating the scatter signal. In a further example, radiography system 202 is arranged for performing the step 104a such that the respective local properties of the radiography image comprise a respective local signal of the radiography image and a respective local spatial gradient of said respective local signal. In another example, radiography system 202 is arranged for performing the step 104a using such scatter kernels that are generated upfront, i.e. prior to execution of the method 100, using Monte Carlo simulation.

In a further example, radiography system 202 is arranged for performing step 106 at a resolution lower than the resolution of the radiography image. Alternatively, radiography system 202 is arranged for performing step 106 at full resolution. In a further specific example, radiography system 202 is arranged for performing a step 108 of increasing the resolution of the estimated scatter signal to a level equal to the resolution of the image.

In another example, radiography system 202 is arranged for performing a step 103 of specifying via segmentation an anatomical area for which contrast enhancement is particularly desired. Radiography system 202 may perform step 103 may be initiated manually, for example via user interface 201, or automatically.

Optionally, radiography system 202 is arranged for performing a step 112 for displaying a corrected radiography image i.e. the radiography image obtainable by the various embodiment of the radiography system.

Figure 3:
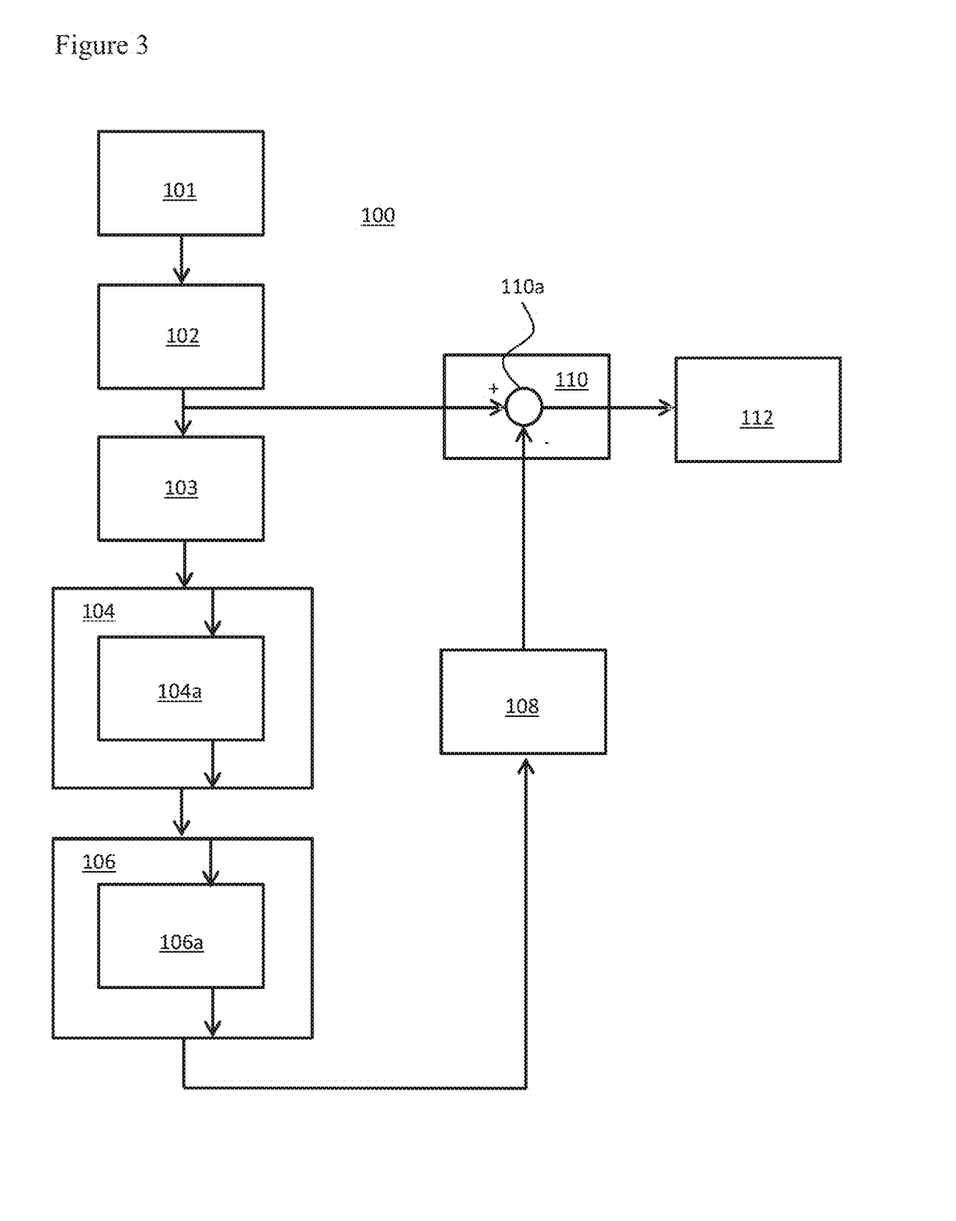
FIG. 3 schematically displays a method performable by an embodiment of the radiography system according to the present invention.

Referring to FIG. 3, in another example radiography system 202 is arranged for performing, as part of the step 110, a step 110a for subtracting the estimated scatter signal from the radiography image. For example, if the scatter signal is zero, step 110a and hence step 110 will not yield any change to the radiography image. In this specific example radiography system 202 is preferably arranged to perform the subtraction in the linear data space. In case the radiography image is available in the logarithmic data space, radiography system 202 is to perform a transformation to the linear data space prior to subtraction, and after such subtraction, radiography system 202 is to perform a transformation back to the logarithmic data space.

Referring to FIG. 4, in another specific example radiography system 202 is arranged for performing, as part of the 110, a step 110b for generating the scatter signal fraction via division of the scatter signal by the radiography image. In this specific example radiography system 202 is furthermore arranged, as part of the step 110, for performing a step 110c for subtracting the scatter signal fraction from 100% (or 1). Radiography system 202 in this specific example is furthermore arranged for performing, as part of the step 110, a step 110d for multiplying the radiography image with the outcome of step 110c. For example, if the scatter signal fraction is zero, the step 110 will not yield any change to the radiography image. In this specific example radiography system 202 is preferably arranged to perform the multiplication in the linear data space. In case the radiography image is available in the logarithmic data space, radiography system 202 is to perform a transformation to the linear data space prior to multiplication, and after such multiplication, radiography system 202 is to perform a transformation back to the logarithmic data space.

Figure 5:
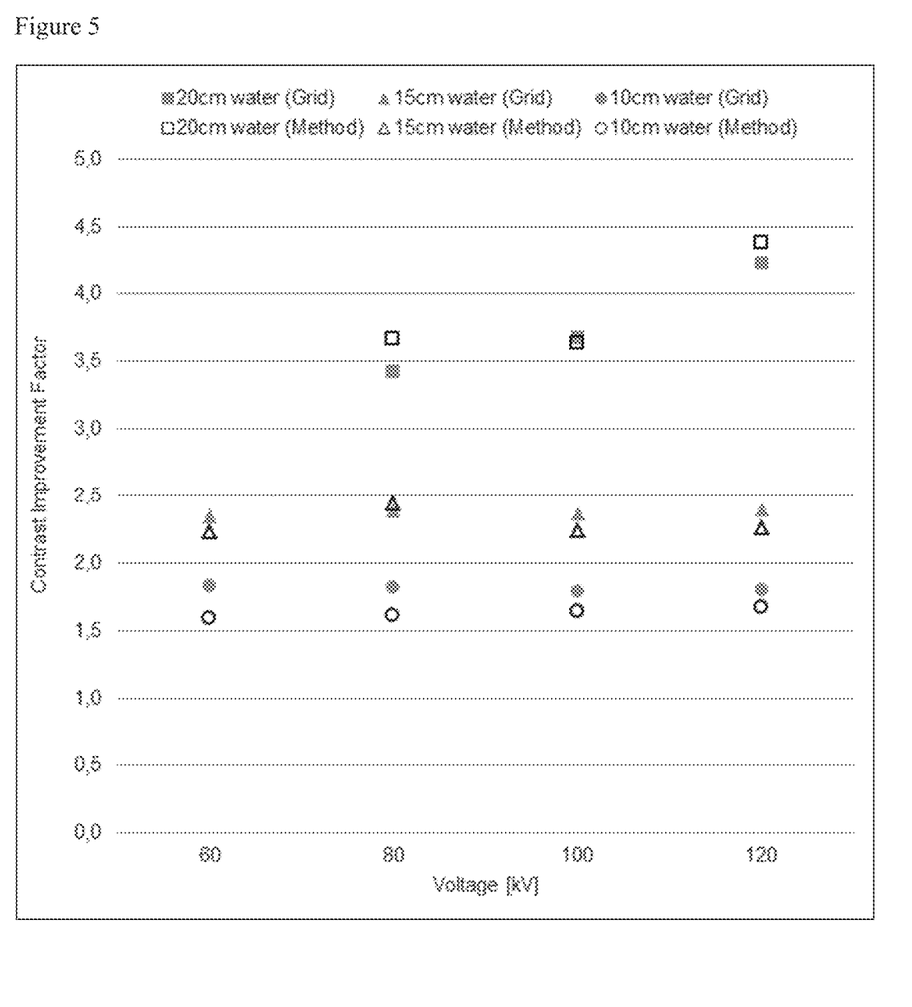
FIG. 5 depicts results of experimental verification of a calibration step performable by an embodiment of the radiography system according to the present invention.

FIG. 5 displays an experimental verification of calibration data, which calibration data in a particular example of radiography system 202 may be employed for performing step 106. More specifically FIG. 5 displays the contrast improvement factor (CIF) as a function of tube voltage for several water heights. Filled symbols as denoted by "Grid" relate to measurements with the reference anti-scatter grid being physically installed; empty symbols as denoted by "Method" relate to measurements with an embodiment of radiography system 202 performing method 100. In this specific example, the reference anti-scatter has selectivity 5.6 and contrast improvement ratio 3.4, both in method 100 and in the measurement with the reference anti-scatter grid being physically installed. For the determination of CIF, an X-ray image is generated of a contrast step generated by an aluminum disc on top of water. Two regions of interest (region of interest hereinafter referred to as ROI) are defined in such image. $ROI_1$, having mean pixel value $level_1$, is outside the attenuated area of the aluminum disc. $ROI_2$, having mean pixel value $level_2$, is inside said area. Contrast C follows from $C=(level_1-level_2)/level_1$. For measurements with the reference anti-scatter grid installed, CIF is denoted as $CIF_{Grid}$ which is defined as $C_{Grid}/C_0$ wherein $C_0$ denotes the reference contrast obtained without using either the reference anti-scatter grid or the embodiment of radiography system 202 performing the method 100. Likewise, for measurements employing the embodiment of radiography system 202 performing method 100, CIF is denoted as CIF$_{Method}$ which is defined as C$_{Method}$/C$_0$. Apparently, for all tube voltages and water heights considered, calibration data are remarkably accurate.

Figure 6:
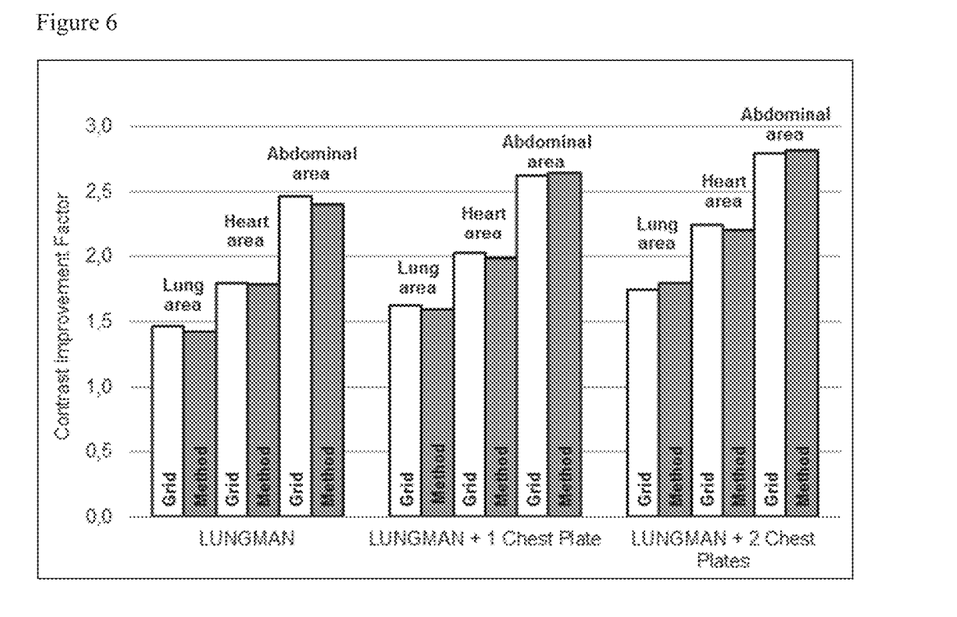
FIG. 6 depicts results of experimental verification of a method performable by an embodiment of the radiography system according to the present invention.

FIG. 6 displays experimental verification of the method 100 using a thorax phantom and more specifically the multipurpose chest phantom "Lungman" by Kyoto Kagagu, Kyoto, Japan. Again measurements were performed with the reference anti-scatter grid being physically installed, as well as measurements employing an embodiment of radiography system 202 performing method 100. Such measurements again are referred to via "Grid" and "Method", respectively. In this particular example, the reference anti-scatter grid has selectivity 5.6 and contrast improvement ratio 3.4. Chest plates were used to mimic patients of different sizes. Aluminum discs, for the purpose of generating a contrast step as explained in relation to FIG. 4, were positioned in the lung, retrocardial and abdominal areas. Aforementioned areas are separately experimentally assessed, see FIG. 6. The agreement between the CIF levels, as obtained with the embodiment of radiography system 202 performing method 100 on the one hand, and by physically employing the reference anti-scatter grid on the other hand, is remarkably strong.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method for processing a radiography image derived from an X-ray radiation passing through an object, comprising acts of:
   estimating, based on the radiography image, a scatter signal present in said radiography image;
   accessing a database to retrieve calibration data previously acquired with a reference anti-scatter device;
   calculating, based on the estimated scatter signal and the retrieved calibration data, a scatter removal signal indicative of a scattered radiation removable from the X-ray radiation passing through the object by the reference anti-scatter device; and
   correcting the radiography image based on the scatter removal signal.

2. A radiography system for processing a radiography image comprising:
   a source configured to provide radiation to a region of interest;
   a detector configured to detect radiation passed through region of interest; and
   a processor coupled to a memory, the memory including instructions that configure the processor to:
      estimate, based on the radiography image, a scatter signal present in said radiography image;
      access a database to retrieve calibration data previously acquired with a reference anti-scatter device;
      calculate, based on the estimated scatter signal and the retrieved calibration data, a scatter removal signal indicative of a scattered radiation removable from the X-ray radiation passing through the object by the reference anti-scatter device; and
      correct the radiography image based on the scatter removal signal.

3. The radiography system according to claim 2, wherein the reference anti-scatter device is a reference anti-scatter grid.

4. The radiography system according to claim 2, further comprising a user interface for specifying a quality of the reference anti-scatter device by a user manual interaction.

5. The radiography system according to claim 2, wherein the instructions further configure the processor to retrieve from the database representative scatter kernels in relation to respective local properties of the radiography image and subsequently superposition said scatter kernels for estimating the scatter signal.

6. The radiography system according to claim 5, wherein the respective local properties of the radiography image comprise a respective local signal of the radiography image and a respective local spatial gradient of said respective local signal.

7. The radiography system according to claim 5, wherein the instructions further configure the processor to generate the scatter kernels upfront by Monte Carlo simulation.

8. The radiography system according to claim 2, wherein the instructions further configure the processor to estimate the scatter signal at a resolution lower than a resolution of the radiography image.

9. The radiography system according to claim 8, wherein the instructions further configure the processor to increase a resolution of the estimated scatter signal to a level equal to the resolution of the radiography image.

10. The radiography system according to claim 2, wherein the instructions further configure the processor to specify via segmentation an anatomical area for which contrast enhancement is desired.

11. The radiography system according to claim 2, wherein the instructions further configure the processor to correct the radiography image by subtracting the estimated scatter signal from the radiography image.

12. The radiography system according to claim 2, wherein the instructions further configure the processor correct the radiography image by multiplying the radiography image with a scatter signal fraction incorporating the estimated scatter signal.

13. A non-transitory computer readable medium comprising computer instructions which, when executed by a processor, configure the processor to process a radiography image by performing acts of:
   estimating, based on the radiography image, a scatter signal present in said radiography image;
   accessing a database to retrieve calibration data previously acquired with a reference anti-scatter device;
   calculating, based on the estimated scatter signal and the retrieved calibration data, a scatter removal signal indicative of a scattered radiation removable from the X-ray radiation passing through the object by the reference anti-scatter device; and
   correcting the radiography image based on the scatter removal signal.

14. The method of claim 1, further comprising an act of receiving a specified quality of the reference anti-scatter device from a user interface.

15. The method of claim 1, further comprising acts of:
retrieving from the database representative scatter kernels in relation to respective local properties of the radiography image; and
superpositioning said scatter kernels for estimating the scatter signal.

16. The method of claim 15, wherein the respective local properties of the radiography image comprise a respective local signal of the radiography image and a respective local spatial gradient of said respective local signal.

17. The method of claim 1, wherein the estimating act estimates the scatter signal at a resolution lower than a resolution of the radiography image.

18. The method of claim 17, further comprising an act of increasing a resolution of the estimated scatter signal to a level equal to the resolution of the radiography image.

19. The method of claim 1, further comprising an act of segmenting an anatomical area for which contrast enhancement is desired.

20. The method of claim 1, wherein the correcting act correct the radiography image by one of subtracting the estimated scatter signal from the radiography image and multiplying the radiography image with a scatter signal fraction incorporating the estimated scatter signal.

\* \* \* \* \*